United States Patent [19]

Bokerman et al.

[11] Patent Number: 5,233,070
[45] Date of Patent: Aug. 3, 1993

[54] PROCESS FOR CONVERTING CHLORINE END-TERMINATED POLYORGANOSILOXANES TO POLYORGANOCYCLOSILOXANES

[75] Inventors: Gary N. Bokerman, Midland, Mich.; Larry H. Wood, Campbellsburg, Ky.

[73] Assignee: Dow Corning Corporation, Midland, Mich.

[21] Appl. No.: 996,417

[22] Filed: Dec. 23, 1992

[51] Int. Cl.$^5$ ................................. C07F 7/08
[52] U.S. Cl. ...................... 556/460; 556/461
[58] Field of Search ................... 556/460, 461

[56] References Cited

U.S. PATENT DOCUMENTS

| | | | |
|---|---|---|---|
| 2,467,976 | 4/1949 | Hyde | 260/448.2 |
| 2,779,776 | 1/1957 | Hyde et al. | 260/448.2 |
| 3,558,681 | 1/1971 | Kuznetsova et al. | 260/448.2 |
| 3,590,064 | 6/1971 | Lacefield | 260/448.2 E |
| 3,607,898 | 9/1971 | Macher | 260/448.2 E |
| 4,412,080 | 10/1983 | Williams | 556/460 |
| 4,423,240 | 12/1983 | Yeboah | 260/448.2 |
| 4,447,630 | 5/1984 | Williams | 556/460 |
| 4,589,420 | 8/1987 | Baile et al. | 556/460 |
| 4,764,631 | 8/1988 | Halni et al. | 556/460 |
| 4,895,967 | 1/1990 | Crivello et al. | 556/460 X |
| 5,068,383 | 11/1991 | Bourgoin et al. | 556/460 X |

*Primary Examiner*—Paul F. Shaver
*Attorney, Agent, or Firm*—William F. Boley

[57] ABSTRACT

The present invention is a process for converting chlorine end-terminated polyorganosiloxanes to polyorganocyclosiloxanes. The process comprises forming a mixture comprising chlorine end-terminated polyorganosiloxanes, aqueous hydrogen chloride, and a heterogeneous reequilibrium catalyst. The mixture is heated at a temperature within a range of about 70° C. to 150° C. to effect reequilibrium of the chlorine end-terminated polyorganosiloxanes to form polyorganocyclosiloxanes which are removed from the process as they are formed.

16 Claims, No Drawings

PROCESS FOR CONVERTING CHLORINE END-TERMINATED POLYORGANOSILOXANES TO POLYORGANOCYCLOSILOXANES

BACKGROUND OF INVENTION

The present invention is a process for converting chlorine end-terminated polyorganosiloxanes to polyorganocyclosiloxanes. The process comprises forming a mixture comprising chlorine end-terminated polyorganosiloxanes aqueous hydrogen chloride, and a heterogeneous reequilibrium catalyst. The mixture is heated at a temperature within a range of about 70° C. to 150° C. to effect reequilibrium of the chlorine end-terminated polyorganosiloxanes to form polyorganocyclosiloxanes which are removed from the process as they are formed.

When the polyorganocyclosiloxanes are removed from the process they are contaminated with chlorine end-terminated polyorganosiloxanes having similar molecular weight. Therefore, in a preferred process the mixture containing the polyorganocyclosiloxanes and chlorine end-terminated polyorganosiloxanes is refluxed to increase the molecular weight of the chlorine end-terminated polyorganosiloxanes to facilitate their recovery. The recovered chlorine end-terminated polyorganosiloxanes can be returned to the process. The described process can provide for conversion of greater than 90 weight percent of the chlorine end-terminated polyorganosiloxanes added to the process to polyorganocyclosiloxanes.

The hydrolysis of an organohalosilane, for example dimethyldichlorosilane, results in a hydrolyzate comprising a mixture of cyclic siloxanes and chlorine end-terminated short-chained polyorganosiloxanes. Much attention has been given in the art to controlling the ratio of cyclic siloxanes to polyorganosiloxane linears in the hydrolyzate. However despite the ability to control the ratio of cyclic siloxanes to linear polyorganosiloxanes in the hydrolyzate, market demand for cyclic siloxanes can exceed production capacity, or, in the process of meeting market demand for cyclic siloxanes an excess of polyorganosiloxanes linears is created.

The present process is a method for converting the chlorine end-terminated polyorganosiloxanes produced during the hydrolysis process into polyorganocyclosiloxanes. The present process is advantageous because it can use as a feed the hydrolyzate containing aqueous hydrogen chloride, chlorine end-terminated polyorganosiloxanes, and polyorganocyclosiloxanes. Unlike other processes for converting linear polyorganosiloxanes to cyclic siloxanes it is not necessary to isolate the chlorine-end terminated polyorganosiloxanes or to perform extensive washing to convert the terminal-chlorine to hydroxyl substitutions. The present process is conducted by heating a mixture comprising chlorine end-terminated polyorganosiloxanes, aqueous hydrogen chloride, and a reequilibration catalyst to effect reequilibration of the chlorine end-terminated polyorganosiloxanes to polyorganocyclosiloxanes which are removed from the reaction zone as they are formed.

The acid catalyzed reequilibration of linear polydimethylsiloxanes is known. For example, Hyde, U. S. Pat. No. 2,467,976, issued Apr. 19, 1949, describes a method for increasing the average molecular weight of a completely dehydrated polydimethylsiloxane by refluxing with hydrochloric acid. Hyde et al., U. S. Pat. No. 2,779,776, issued Jan. 29, 1957 teaches that the equilibrium reaction between a siloxane and aqueous acid is reversible and the polymer size of the siloxane at the point of equilibrium of the reversible reaction is determined by the concentration of acid in the aqueous phase.

Catalyzed, non-aqueous, systems for converting hydroxy-terminated polyorganosiloxanes to polyorganocyclosiloxanes are also known. Macher, U. S. Pat. No. 3,607,898, issued Sep. 21, 1971, describes a process where dried polymethylvinylsiloxane is heated in the presence of lithium hydroxide and a co-catalyst selected from a group consisting of alkyl polyethers and triphenylphosphine oxide. The resultant product is reported to be cyclic symtetramethyltetravinyltetrasiloxane. Lacefield, U. S. Pat. No. 3,590,064, issued Jun. 29, 1971, describes a non-aqueous process for preparing cyclic siloxanes where a halogen endblocked linear polysiloxane is reacted with at least a stoichiometric amount of an alkali metal carbonate salt in the presence of a suitable polar solvent. Kuznetsova et al., U. S. Pat. No. 3,558,681, issued Jan. 26, 1971, describes a process for making cyclic siloxanes by the thermal degradation of hydroxyl-terminated methylphenylsiloxanes contacted with lithium hydroxide or lithium silanolate.

Aqueous processes for forming polyorganocyclosiloxanes from chlorine-end terminated polyorganosiloxanes are also known. Yeboah, U. S. Pat. No. 4,423,240, describes a process where dimethyldichlorosilane is hydrolyzed in the presence of aqueous hydrochloric acid and an anionic surfactant, for example sodium lauryl sulfate, to shift the equilibrium to higher yields of polyorganocyclosiloxanes. Yeboah reports yield for the polyorganocyclosiloxanes within a range of 70 to 78 weight percent. Williams, U. S. Pat. No. 4,412,080, issued Oct. 25, 1983, reports a process for preparing polyorganocyclosiloxanes, where dimethyldichlorosilane is hydrolyzed in the presence of aqueous hydrogen chloride and a homogeneous catalyst comprising normal C6-16 alkyl sulfonic acid. This catalyst also acts as a surfactant leading to a shift of the process equilibrium to favor cyclics. The process is run as a batch process with typical yields reported to be in the range of about 63 to 89 percent cyclics. Williams, U. S. Pat. No. 4,447,630, issued May 8, 1984, describes a method of making polyorganocyclosiloxanes by hydrolyzing diorganodichlorosilanes and aqueous hydrochloric acid in the presence of a perfluorinated alkyl substituted organic material such as a perfluorinated alkyl sulfonic acid salt. In this process, the perfluorinated alkyl sulfonic acid is a homogeneous catalyst which acts as a surfactant to shift the equilibrium in favor of polyorganocyclosiloxanes. This process is reported to give yields of as high as 97 percent cyclics.

Baile et al., U. S. Pat. No. 4,689,420, issued Aug. 25, 1987, reports a process for converting polydiorganosiloxanes to polydiorganocyclosiloxanes. The process comprises (A) feeding a mixture of polydiorganosiloxanes, a catalyst, and an organic solvent to a device in which water is formed as the polydiorganosiloxanes react in the presence of the catalyst and the organic solvent, the water formed being driven out of the device as a two-phase organic solvent/water azeotrope; (B) reacting the polydiorganosiloxane-catalyst-solvent mixture from (A), essentially free of water, to convert the polydiorganosiloxanes to the desired product polydiorganocyclosiloxanes; and (C) recovering the desired product polydiorganocyclosiloxanes. Useful catalyst were reported to be alkali metal hydroxides and alkali metal silanolates. Baile et al. report that in their process the presence of water during the rearrangement reaction shifted the chemical equilibrium away from the product cyclic siloxanes in favor of linear polydiorganosiloxanes.

SUMMARY OF INVENTION

The present invention is a process for converting chlorine end-terminated polyorganosiloxanes to polyorganocyclosiloxanes. The process comprises forming a mixture comprising chlorine end-terminated polyorganosiloxanes, aqueous hydrogen chloride, and a heterogeneous reequilibrium catalyst. The mixture is heated at a temperature within a range of about 70° C. to 150° C. to effect reequilibrium of the chlorine end-terminated polyorganosiloxanes to form polyorganocyclosiloxanes which are removed from the process as they are formed.

DESCRIPTION OF INVENTION

The present invention is a process for converting chlorine end-terminated polyorganosiloxanes to polyorganocyclosiloxanes. The process comprises:

(A) forming a mixture comprising a chlorine end-terminated polyorganosiloxane described by formula $$Cl(R_2SiO)_nSiR_2Cl,\qquad(1)$$

aqueous hydrogen chloride, and a heterogeneous reequilibrium catalyst selected from a group consisting of activated carbon, acid clay, and sulfonic acid resin;

(B) heating the mixture at a temperature within a range of about 70° C. to 150° C. to effect reequilibrium of the chlorine end-terminated polyorganosiloxanes; and (C) continuously recovering polyorganocyclosiloxanes described by formula $$(R_2SiO)_x;\qquad(2)$$

where each R is independently selected from a group consisting of hydrogen atoms, monovalent hydrocarbon radicals comprising from one to 18 carbon atoms, and substituted monovalent hydrocarbon radicals comprising from one to 18 carbon atoms, $n=1$ to 50, and $x=3$ to 20.

The present process can be run as a batch process, a semi-batch process, or as a continuous process in standard type reactors suitable for reacting chlorosilanes. The reactor can be, for example, a fixed-bed reactor, a stirred-bed reactor, or a fluidized-bed reactor.

The mixture comprising the chlorine end-terminated polyorganosiloxane, aqueous hydrogen chloride, and heterogeneous reequilibrium catalyst can be formed by standard means. For example, the chlorine end-terminated polyorganosiloxane and aqueous hydrogen chloride can be fed separately or as a mixture of the two to a reactor containing the heterogeneous reequilibrium catalyst.

Chlorine end-terminated polyorganosiloxanes useful in the present process are described by formula (1). The chlorine end-terminated polyorganosiloxanes have substituents R, where each substituent R is independently selected from a group consisting of hydrogen atoms, monovalent hydrocarbon radicals comprising from one to 18 carbon atoms, and substituted monovalent hydrocarbon radicals comprising from one to 18 carbon atoms. When R is a hydrogen atom, it is preferred that no more than one hydrogen atom be bonded to each silicon. When R is a monovalent hydrocarbon radical, R can be for example, methyl, ethyl, propyl, tert-butyl, isobutyl, vinyl, allyl, phenyl, and cyclopentyl. When R is a substituted monovalent hydrocarbon, R can be for example, chloromethyl, 3,3,3-trifluoropropyl, or perfluoropropyl. Preferred is when each R is independently selected from a group consisting of hydrogen atom, methyl, vinyl, and phenyl. Most preferred is when R is methyl. The chlorine end-terminated polyorganosiloxane described by formula (1) contains n number of siloxy units of formula $-(R_2SiO)-$, where n can be a value from one to 50. Preferred is where n is a value from about 3 to 20.

The chlorine end-terminated polyorganosiloxane is reequilibrated in the present process in the presence of aqueous hydrogen chloride. In general, the concentration of hydrogen chloride in the aqueous phase can be within a range of about 10 weight percent to about 42 weight percent. Preferred is when the concentration of hydrogen chloride in the aqueous phase is within a range of about 20 weight percent to about 32 weight percent. Those skilled in the art will recognize that a result of the reequilibrium process is the generation of hydrogen chloride. Therefore, the desired concentration of hydrogen chloride in the aqueous phase can be achieved by adding water to the process and generating the hydrogen chloride in situ or by adding a preformed aqueous solution of hydrogen chloride to the process.

The water and hydrogen chloride present process aids in the removal of polyorganocyclosiloxanes by increasing the vapor flow in the reactor. In addition the heterogeneous reequilibrium catalysts employed in the present process require small amounts of water to keep them active, with the optimal amount of water being specific to the catalyst. Too much water can deactivate the catalyst. Therefore, the amount of water employed in the process will depend upon the specific catalyst. Generally it has been found, for example, when the heterogeneous catalyst is activated carbon a useful volume of water is where the volume of water is within a range of about 5 volume percent to 200 volume percent of the chlorine end-terminated polyorganosiloxanes added to the process. When the heterogeneous catalyst is activated carbon, a preferred volume of water is within a range of about 80 volume percent to 120 volume percent of the chlorine end-terminated polyorganosiloxanes added to the process.

The heterogeneous reequilibrium catalyst employed in the present process is selected from a group consisting of activated carbon, acid clays, and sulfonic acid resins. The heterogeneous reequilibrium catalyst can be in the form of, for example, particles, powders, flakes, chips, or pellets. Any activated carbon capable of facilitating the reequilibrium of chlorine end-terminated polyorganosiloxanes can be used in the present process. The activated carbon useful in the present process can be of the thermal or chemical activated type.

Any acid clay capable of facilitating the reequilibrium of chlorine end-terminated polyorganosiloxanes can be used in the present process. The acid clays can be, for example, those produced from halloysites, kaolinites, and bentonites composed of montmorillonite; where the clay is treated with an acid solution, for example, sulfuric acid.

Any sulfonic acid resin capable of facilitating the reequilibrium of chlorine end-terminated polyorganosiloxanes can be used in the present process. The sulfonic acid resin can be, for example, a synthetic resin having —SO$_3$H or —SO$_2$OH groups attached thereto. The sulfonic acid resin can be, for example, Amberlyst A15 (Rhom and Haas, Philadelphia. PA) or Dowex DR2040 (The Dow Chemical Company, Midland, MI).

The amount of heterogeneous reequilibrium catalyst employed in the present process can be varied within wide limits in relation to the chlorine end-terminated polyorganosiloxane added to the process. The amount of heterogeneous reequilibrium catalyst will depend upon such factors as the type of catalyst, the specific chlorine end-terminated polyorganosiloxane to be reequilibrated, the process temperature, and the amount of water and hydrogen chloride concentration. Generally the process is limited by mass transfer, therefore the larger the amount of heterogeneous reequilibrium catalyst employed in the process the faster reequilibrium is established. Examples of useful amount of catalyst are provided in the Examples provided herein.

The mixture comprising the chlorine end-terminated polyorganosiloxane, aqueous hydrogen chloride, and heterogeneous reequilibrium catalyst is heated at a temperature within a range of about 70° C. to 150° C. to effect reequilibrium of the chlorine end-terminated polyorganosiloxanes to polyorganocyclosiloxanes. Higher temperatures may be used but may result in reduce yield of the desired polyorganocyclosiloxanes as a result of, for example, scission of organic groups from silicon. Lower temperatures may also be used but may make the reequilibrium time too long for practical commercial application. A preferred temperature for running the present process is within a range of about 90° C. to 130° C.

Polyorganocyclosiloxanes as described by formula (2) are continuously recovered from the process. The polyorganocyclosiloxanes have substituent R, where R is as previously described for the chlorine end-terminated polyorganosiloxanes. The polyorganocyclosiloxanes have a degree of polymerization (dp) described by the value x, where x=3 to 20. The preferred polyorganocyclosiloxanes are those in which x=3 to 5. The most preferred polyorganocyclosiloxanes are those where each R is methyl and x=3 to 5.

The continuous recovery of polyorganocyclosiloxanes from the process can be effected by standard means. By "continuous recovery of polyorganocyclosiloxanes," it is meant that the polyorganocyclosiloxanes are removed from the reactor as they are formed. For example the process can be run at a temperature sufficient to cause vaporization of the desired polyorganocyclosiloxanes and the resultant vapor continuously removed from the reactor. If desired a carrier gas, non-detrimental to the process, can be used in the reactor to facilitate removal of the polyorganocyclosiloxanes. In a preferred process, the amount of water in the process is controlled such that water vapor serves as a carrier gas to facilitate removal of the polyorganocyclosiloxanes from the reactor.

Typically, as the polyorganocyclosiloxanes are continuously recovered from the present process there is also recovered therewith chlorine end-terminated polyorganosiloxanes having a similar boiling point. In a preferred process, the recovered polyorganocyclosiloxanes are separated from the chlorine end-terminated polyorganosiloxanes having a similar boiling point by hydrolysis of the chlorine end-terminated polyorganosiloxanes to higher molecular weight polyorganosiloxanes. These higher molecular weight polyorganosiloxanes can then be separated from the desired polyorganocyclosiloxanes by standard methods, for example, distillation. The higher molecular weight polyorganosiloxanes can then be returned to the process for further reequilibration to desired polyorganocyclosiloxanes.

The following examples are provided to illustrate the present invention. These examples are not intended to limit the present claims.

EXAMPLE 1

Polydimethylcyclosiloxanes were formed by heating chlorine end-terminated polydimethylsiloxanes in the presence of activated carbon and aqueous hydrogen chloride. The reactor in which the process was conducted comprised a 250 mL three-necked round bottom flask. One neck of the reactor was equipped with a thermometer, a second neck with an addition funnel for addition of aqueous hydrogen chloride to the process, and the third neck was connected to a Barrett distilling receiver. The Barrett distilling receiver was further connected to a condenser for collecting distillate to the distilling receiver. To the reactor was added 75 gm of activated carbon (Calgon, Pittsburg, PA), 100 gm of chlorine end-terminated polydimethylsiloxanes having an average dp of about thirty-three, and 100 ml of a 37 weight percent aqueous hydrogen chloride solution. The reactor was heated to about 110° C. and maintained at this temperature during the ensuing five hour sampling period. During conduct of the process, the reactor was visually observed and additional 37 weight percent aqueous hydrogen chloride added to maintain approximately an equal volume of siloxanes and aqueous hydrogen chloride within the reactor. A mixture of aqueous hydrogen chloride, cyclic siloxanes, and linear siloxanes evolved from the reactor into a distilling receiver. The cyclic and linear siloxanes recovered in the distilling receiver were separated from the aqueous hydrogen chloride by phase separation and decantation and analyzed by supercritical fluid chromatography (SFC). The results provided in Table 1 are expressed as the weight percent each cyclic siloxane represents of the total cyclic and linear siloxanes evolved from the process at the indicated times. The term "D" represents a polydimethycyclosiloxane and the number associated with the term D indicates the number of silicon atoms present in the polydimethycyclosiloxane. The column labelled "Total Cyclics" is the weight percent of all cyclics recovered from the process and includes those cyclics comprising more than six silicon atoms. The molecular number (Mn) for the linear siloxanes is also provided in Table 3.

TABLE 1

Reequilibration of Chlorine End-Terminated Polydimethyl-Siloxanes to Polydimethylcyclosiloxanes

| | Weight percent | | | | | |
|---|---|---|---|---|---|---|
| Time(h) | D3 | D4 | D5 | D6 | Total Cyclics | Linear Mn |
| 0.5 | 3.0 | 57.7 | 27.2 | 7.0 | 97.6 | 498 |
| 1.0 | 3.5 | 52.6 | 28.2 | 8.2 | 95.4 | 490 |
| 2.0 | 2.4 | 51.4 | 29.3 | 8.2 | 93.8 | 684 |
| 3.0 | 4.0 | 41.7 | 27.5 | 10.9 | 90.2 | 738 |
| 4.0 | 2.9 | 42.2 | 10.9 | 11.9 | 93.2 | 931 |

EXAMPLE 2

A hydrolyzate prepared by reacting dimethyldichlorosilane with aqueous hydrogen chloride in the presence of activated carbon was further reacted in a process similar to that described in Example 1. To the reactor described in Example 1 was added 75 g of activated carbon (as previously described), 100 g of dimethyldichlorosilane, and 100 ml of 37 weight percent aqueous hydrogen chloride. The resultant reaction was allowed to go to completion. The reaction flask containing the hydrolyzate was then heated to 110° C. and the process conducted similar to that described in Example 1. The collected samples were analyzed by SFC as previously described. The results are reported in Table 2, with the headings of Table 2 the same as described for Table 1.

TABLE 2

Reequilibration of Chlorine End-Terminated Polydimethyl-Siloxane Hydrolyzate to Polydimethylcyclosiloxanes

| Time(h) | Weight percent | | | | Total Cyclics | Linear Mn |
|---|---|---|---|---|---|---|
| | D3 | D4 | D5 | D6 | | |
| 0.5 | 1.4 | 66.4 | 23.9 | 4.0 | 96.4 | 1569 |
| 1.0 | 2.0 | 60.9 | 24.7 | 5.8 | 94.9 | 1600 |
| 2.0 | 4.7 | 58.8 | 21.7 | 5.2 | 91.9 | 1126 |

We claim:

1. A process for converting chlorine end-terminated polyorganosiloxanes to polyorganocyclosiloxanes, the process comprising:

(A) forming a mixture comprising a chlorine end-terminated polyorganosiloxane described by formula $$Cl(R_2SiO)_nSiR_2Cl,$$

aqueous hydrogen chloride, and a heterogeneous reequilibrium catalyst selected from a group consisting of activated carbon, acid clays, and sulfonic acid resins:

(B) heating the mixture at a temperature within a range of about 70° C. to 150° C. to effect reequilibrium of the chlorine end-terminated polyorganosiloxanes; and (C) continuously recovering polyorganocyclosiloxanes described by formula $$(R_2SiO)_x;$$

where each R is independently selected from a group consisting of hydrogen atoms, monovalent hydrocarbon radicals comprising from one to 18 carbon atoms, and substituted monovalent hydrocarbon radicals comprising from one to 18 carbon atoms. $n=1$ to 50, and $x=3$ to 20.

2. A process according to claim 1, where each R is independently selected from a group consisting of hydrogen atom, methyl, vinyl, and phenyl.

3. A process according to claim 1, where each R is methyl

4. A process according to claim 1, where $n=3$ to 20.

5. A process according to claim 1, where concentration of hydrogen chloride in the aqueous hydrogen chloride is within a range of about 10 weight percent to about 42 weight percent.

6. A process according to claim 1, where concentration of hydrogen chloride in the aqueous hydrogen chloride is within a range of about 20 weight percent to about 32 weight percent.

7. A process according to claim 1, where the heterogeneous reequilibrium catalyst is activated carbon and water present in the process is within a range of about 80 volume percent to 120 volume percent of the chlorine end-terminated polyorganosiloxanes added to the process.

8. A process according to claim 1, where the heterogeneous catalyst is a sulfonic acid resin selected from a group consisting of Amberlyst A15 and Dowex DR2040.

9. A process according to claim 1, where the temperature is within a range of about 90° C. to 130° C.

10. A process according to claim 1, where $x=3$ to 5.

11. A process according to claim 10, where each R is methyl.

12. A process according to claim 1, where water present in the process is controlled such that water vapor serves as a carrier gas to facilitate removal of the polyorganocyclosiloxanes from the process.

13. A process according to claim 1, where the heterogeneous reequilibrium catalyst is activated carbon.

14. A process according to claim 1, where the heterogeneous reequilibrium catalyst is an acid clay.

15. A process according to claim 1, where the heterogeneous reequilibrium catalyst is a sulfonic acid resin.

16. A process according to claim 1, where the heterogeneous reequilibrium catalyst is activated carbon, each R is methyl, $n=3$ to 20, $x=3$ to 5, the temperature is within a range of about 90° C. to 130° C. concentration of hydrogen chloride in the aqueous hydrogen chloride is within a range of about 20 weight percent to about 32 weight percent, and water present in the process is within a range of about 80 volume percent to 120 volume percent of the chlorine end-terminated polyorganosiloxanes added to the process.

* * * * *